(12) United States Patent
Gallagher

(10) Patent No.: US 9,932,552 B2
(45) Date of Patent: Apr. 3, 2018

(54) LATERAL CIRCULATOR AND AGITATOR FOR POND CULTIVATION

(71) Applicant: Brian J. Gallagher, Los Angeles, CA (US)

(72) Inventor: Brian J. Gallagher, Los Angeles, CA (US)

(*) Notice: Subject to any disclaimer, the term of this patent is extended or adjusted under 35 U.S.C. 154(b) by 0 days.

(21) Appl. No.: 15/354,925

(22) Filed: Nov. 17, 2016

(65) Prior Publication Data

US 2017/0145364 A1 May 25, 2017

Related U.S. Application Data

(60) Provisional application No. 62/257,578, filed on Nov. 19, 2015.

(51) Int. Cl.
*C12M 1/00* (2006.01)
*C12M 1/06* (2006.01)
(Continued)

(52) U.S. Cl.
CPC ............. *C12M 23/18* (2013.01); *A01G 33/00* (2013.01); *B01F 5/108* (2013.01);
(Continued)

(58) Field of Classification Search
None
See application file for complete search history.

(56) References Cited

U.S. PATENT DOCUMENTS

| 336,126 A | 2/1886 | Ludlum |
| 2,986,387 A * | 5/1961 | Illing ...................... F27B 9/243 |
| | | 110/269 |

(Continued)

FOREIGN PATENT DOCUMENTS

| CN | 203095654 U | 7/2013 |
| CN | 103184141 B | 4/2016 |

(Continued)

OTHER PUBLICATIONS

Eng. MT—Jeong, Seok Man. Sporting goods using water tank. Korean Patent Application Publication No. 10-2005-0013027. Publication Date: Feb. 2, 2005. specif. pp. 1, 2, 4.*

(Continued)

*Primary Examiner* — Renee Claytor
*Assistant Examiner* — Sharon M. Papciak
(74) *Attorney, Agent, or Firm* — PatentBest; Andrew McAleavey

(57) ABSTRACT

A lateral circulator for generating agitation or circulation in a cultivation pond is disclosed. The circulator comprises at least a drive pulley and a secondary pulley, both oriented vertically and placed in the pond separated from one another along the length of the pond. The drive pulley is coupled to a motor, or to a drive train that is itself coupled to the motor. An endless belt is trained over the drive pulley and the secondary pulley. A plurality of cleats is provided along the exterior of the belt. The cleats are typically angled and serve to drive water as the belt rotates through the water. Typically, the belt would extend over much of the length of the cultivation pond, providing agitation and circulation over an extensive, continuous area of the cultivation pond.

8 Claims, 7 Drawing Sheets

(51) Int. Cl.
*A01G 31/00* (2018.01)
*B01F 13/00* (2006.01)
*B01F 5/10* (2006.01)
*A01G 33/00* (2006.01)

(52) U.S. Cl.
CPC ......... *B01F 13/0015* (2013.01); *C12M 27/02* (2013.01); *B01F 2215/0073* (2013.01)

(56) References Cited

U.S. PATENT DOCUMENTS

| | | | |
|---|---|---|---|
| 3,855,370 | A | 12/1974 | Dodd |
| 4,011,939 | A | 3/1977 | Conrad |
| 4,143,759 | A | 3/1979 | Paradis |
| 4,217,728 | A | 8/1980 | Shimamatsu et al. |
| 6,024,209 | A | 2/2000 | Nolte |
| 8,162,769 | B2 | 4/2012 | Henry |
| 8,752,329 | B2 | 6/2014 | Parsheh et al. |
| 9,260,685 | B2 | 2/2016 | Herzog |
| 9,267,102 | B2 | 2/2016 | Osterloh |
| 2006/0105645 | A1* | 5/2006 | Lawson ................ B63H 20/32 440/38 |
| 2010/0279389 | A1 | 11/2010 | Ziller |
| 2015/0275161 | A1 | 10/2015 | Gressel et al. |
| 2016/0029579 | A1 | 2/2016 | Carscallen et al. |
| 2016/0272427 | A1 | 9/2016 | Kaeb et al. |

FOREIGN PATENT DOCUMENTS

| | | | |
|---|---|---|---|
| EP | 1153714 | B1 | 3/2005 |
| FR | 2957750 | | 9/2011 |
| JP | 2007129972 | | 5/2007 |
| KR | 1020050013027 | * | 2/2005 |
| KR | 1020160000687 | | 2/2016 |
| RU | 2596017 | | 8/2016 |
| TW | 200706824 | | 8/2005 |

OTHER PUBLICATIONS

Copenheaver, Blaine R., International Search Report and Written Opinion of the International Searching Authority, or the Declaration for Application No. PCT/US2016/06201. dated Nov. 17, 2016.

Lazur, A., et al, Pond Recirculating Production Systems, Southern Regional Aquaculture Center, SRAC Publication No. 455, Stoneville, Mississipi, Nov. 1997.

* cited by examiner

LATERAL CIRCULATOR AND AGITATOR FOR POND CULTIVATION

CROSS-REFERENCE TO RELATED APPLICATIONS

This application claims priority to U.S. Provisional Patent Application No. 62/257,578, filed Nov. 19, 2015, the contents of which are incorporated by reference in their entirety.

BACKGROUND OF THE INVENTION

1. Field of the Invention

The invention relates generally to circulating and agitating equipment for pond cultivation, and more particularly, to a circulator and agitator for cultivating algae.

2. Description of Related Art

From time immemorial to the present, humans have cultivated microorganisms—sometimes for processes like fermentation, and sometimes to create a biomass from which nutrients and other valuable chemicals can be extracted. While classic fermentation processes—for example, to produce alcohol or to leaven bread—often rely on simple eukaryotes like *S. cerevisiae*, over the last few decades, a great deal of attention has been focused on the cultivation of algae.

Algae is a general term for a diverse group of autotrophic, photosynthetic organisms, most of which are aquatic. These organisms may be cultivated for a variety of reasons, and to generate a variety of end products. For example, algae have become an important source of the so-called "omega-3" fatty acids, which are important in human nutrition. Algae are also cultivated to extract their oils, which can be processed into biodiesel and other forms of fuel. Beyond products and byproducts, cultivated algae can also be used in processes like wastewater treatment.

Cultivation of algae can be done in any number of ways, but is typically done in long, shallow ponds of water. Among other things, most cultivation ponds include an agitator or circulator to circulate the water. In a still pond, the water may stratify, with deeper water having less dissolved oxygen than water nearer the surface, and other nutrients and treatments may not reach the entire volume of the pond, leading to uneven algae growth and reduced yield. The agitator or circulator addresses these issues. Additionally, agitation or circulation can ensure that most of the algae get periodic exposure to strong sunlight, as they are brought toward the surface, followed by darker periods as they sink back toward the bottom, a light-dark pattern that has been found by some researchers to be beneficial. Beyond specific effects on algae, water circulation also maintains homogeneity of the water-nutrient mixture, and can help prevent putrefaction and reduce the growth of unwanted, invasive organisms.

For many decades, the paddlewheel has been the typical agitator used in cultivation ponds. An example of this can be found in U.S. Pat. No. 4,217,728 to Shimamatsu et al., a 1980 patent, the contents of which are incorporated by reference in their entirety. While a paddlewheel does provide agitation, it is a point source; it drives the water in the pond from a single location. In order to provide agitation for an entire pond—which may be quite large—paddlewheel agitation both uses and wastes a large amount of energy, and may not provide uniform agitation over the entire volume of the pond.

SUMMARY OF THE INVENTION

One aspect of the invention relates to a lateral circulator for a cultivation pond. The lateral circulator comprises at least one drive pulley oriented vertically, at least one second pulley, also oriented vertically, and an endless belt trained over the pulleys and oriented such that its breadth extends vertically. The belt has a series of cleats attached to it, typically arranged at a regular pitch and angled at an angle between 0° and 90°, for example, between 10° and 45°. In use, the circulator would typically be positioned in the center of a cultivation pond, leaving approximately equal channel widths on either side and, in most cases, at the ends.

Another aspect of the invention relates to methods for circulating water in cultivation ponds. These methods comprise circulating water in a cultivation pond using an endless belt trained over at least one driving pulley and at least one driven pulley such that the breadth of the belt extends vertically along a substantial portion of the length of the cultivation pond. The belt thus provides circulation not as a point source, but as a continuous source that extends over much of the cultivation pond. Because of the extent of the circulator, in many embodiments, relatively slow velocities of the belt are sufficient to create turbulent lateral circulation (i.e., between the belt and the sidewalls of the cultivation pond), which may reduce power requirements.

Other aspects, features, and advantages of the invention will be set forth in the following description.

BRIEF DESCRIPTION OF THE DRAWING FIGURES

The invention will be described with respect to the following drawing figures, in which like numerals represent like features throughout the description, and in which.

DETAILED DESCRIPTION

Figure 1:
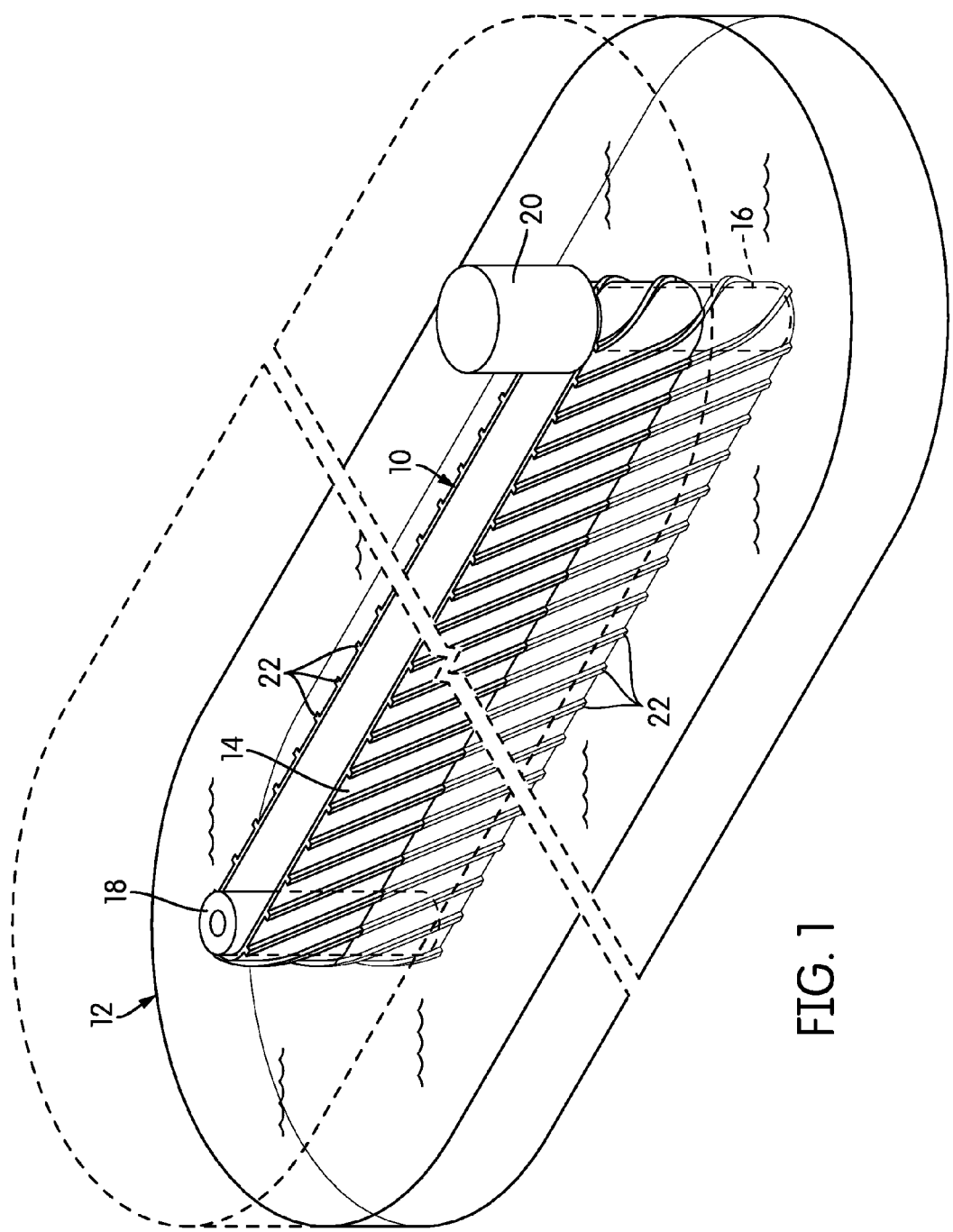
FIG. 1 is a perspective view of a cultivation pond with a continuous lateral circulator according to one embodiment of the invention.

FIG. 1 is a perspective view of a continuous lateral circulator, generally indicated at 10, installed within a cultivation pond 12. The continuous lateral circulator 10 has the general form of a conveyor belt turned on its side, such that the breadth of the belt 14 extends vertically. The belt 14 is endless and is trained over two vertically-extending pulleys 16, 18. A motor 20 coupled to one of the pulleys 16 drives the belt 14 in a loop. A series of angled cleats 22, arranged at a regular pitch along the length of the belt 14, help to push the water in the pond as the belt 14 is driven.

The pond 12 itself is typical for a cultivation pond, and as can be seen in FIG. 1, the circulator 10 is installed in the center of it and extends substantially the entirety of the length of the pond 12, evenly spaced between the sides and the two ends. For example, if the pond 12 is 1,000 feet (305 meters) long and 100 feet (30 meters) wide, the circulator 10 may be approximately 900 feet long, leaving an equal distance at each end. Of course, the circulator 10 need not be perfectly centered in the pond 12 in all embodiments, and ponds 12 may be of any size. As will be described below in more detail, one advantage of circulators 10 according to embodiments of the present invention is that they may remove agitation-based size restrictions on cultivation ponds 12, thereby allowing for larger ponds. The pond 12 may be of any depth, although typical cultivation ponds are relatively shallow—depths of less than 1 foot (0.3 meters) are common.

As shown in FIG. 1, the circulator 10 in the illustrated embodiment is taller than the illustrated depth or water level of the pond 12 in which it is placed. That is, the illustrated water level in the pond 12 is lower than the top of the belt 14 and pulleys 16, 18. In most embodiments, the circulator 10 will extend at least substantially the entire depth of the pond 12, and in many of those embodiments, the circulator 10 may be taller than the average expected pond depth. The extra height allows the water level in the pond 12 to be increased, as might be done for temperature control and for various other reasons known to those skilled in the art. As one example, if a typical water height of a pond 12 is about 12 inches (30 cm), the circulator may be about 18 inches (46 cm) tall. While the cultivation pond 12 illustrated in FIG. 1 is uncovered and open, cultivation ponds 12 may be covered and closed, as is known in the art.

There is no particular limitation to the height of the belt 14 and its pulleys 16, 18, or to the length of the belt 14. Particularly with long belts, it may be helpful to include idler pulleys or rollers, also oriented vertically, which would provide support along the length of the belt 14. Additionally, the circulator 10 may include belt tensioners and other such devices. The length of the belt 14, its height, and the speed at which it is to be driven are among the factors that dictate how much power is required to drive the belt 14. In the illustrated embodiment, a motor 20 directly drives one of the pulleys 16 to move the belt 14. That motor 20 may, in some embodiments, be as small as ½ horsepower or, in other embodiments, as large as 10 horsepower. The placement of the motor 20, however, is not critical. In some embodiments, the motor 20 may be placed on the other pulley 18. In yet other embodiments, the motor 20 may be located elsewhere, and one or both pulleys 16, 18 may be driven by a drive-train connected between the motor 20 and the pulleys 16, 18. Generally speaking, various methods of driving conveyor belts are known, and any compatible method may be used in embodiments of the present invention.

In FIG. 1, the circulator 10 is relatively narrow, with nothing between the two sides of the belt 14. That may not be the case in some embodiments. In some cases, the belt 14 may be arranged around a berm, wall, or other structure, with more pulleys or rollers, if needed, to dictate its path around that structure. For example, many cultivation ponds have walls and other dividing structures, and a belt 14 may be arranged around those walls and structures. As another example, a belt 14 may be placed around a pair of parallel walls that are about as high as the belt 14 and are spaced from each other at a distance of about 3 feet (1 meter). Such walls could be used, for example, to support an elevated horizontal walkway, located between the two sides of the belt 14, that allows maintenance workers to walk along the center of the pond 12 in order to service the circulator 10 or the pond 12 itself.

Additionally, while the belt 14 of FIG. 1 is trained over the pulleys 16, 18 such that it has two long sides that are parallel to one another, that need not be the case in other embodiments. Instead, the belt 14 may be trained over any number of pulleys, rollers, idlers, and other structures to have any desired shape, e.g., polygonal or serpentine, if the geometry of the cultivation pond or other factors dictate it.

Figure 2:
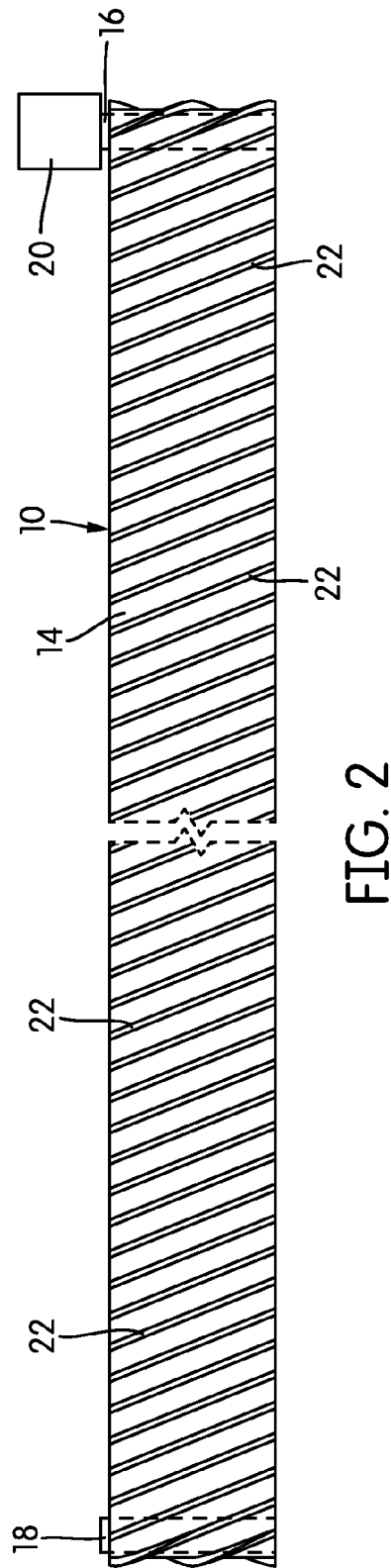
FIG. 2 is an elevational view of the lateral circulator of FIG. 1 in isolation.

FIG. 2 is a side elevational view of the circulator 10 in isolation. In FIG. 2, the evenly-spaced cleats 22 can be seen. Cleats 22 are used to drive the water in the pond 12. In the illustrated embodiment, each cleat 22 is a continuous bar of constant cross-section that extends across the height of the belt 14 at an angle. The cleats 22 of the illustrated embodiment overlap such that if one draws a straight line down the belt 14, that line may intersect several cleats 22, e.g., 4-6 cleats, depending on their number and angle. The cleats 22 are arranged at a regular pitch, which will vary from embodiment to embodiment, but may be on the order of, e.g. 3-6 inches. It should be understood that for reasons of legibility and ease in illustration, the drawing figures show fewer cleats at a greater pitch than would be used in most typical operational embodiments.

Figure 3:
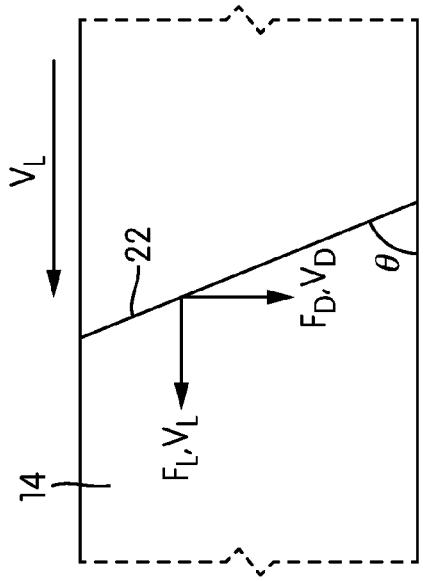
FIG. 3 is a cross-sectional view of one of the cleats on the lateral circulator of FIG. 1.

FIG. 3 is a cross-sectional view of one of the cleats 22. As shown, it has a generally trapezoidal cross-section in the illustrated embodiment, such that it is narrower at the top (i.e., the outermost point) than it is at the base. In a typical embodiment, a cleat 22 might have a height in the range of about 1-2 inches (2.5-5 centimeters), and a width in that range as well. The cleat 22 of FIG. 3 has a base of about 1 inch (2.5 centimeters) and an outward extent of about 2 inches (5 centimeters). It may be helpful if the cleats 22, taken together, have at least the same effective surface contact area as a paddlewheel suitable for use in the same size of cultivation pond 12. ("Effective surface contact area" in this context refers to the area that actually contacts and drives water at any point in time.) In some cases, if numerous cleats 22 are on the belt 14, the effective surface area of those cleats 22 may be greater than that of a paddlewheel that would be used in the same pond, which may allow the belt 14 to move more slowly and provide the same quality of effective circulation.

Of course, the cleats 22 may vary in form and arrangement from embodiment to embodiment, depending on any number of factors. For example, the cleats may instead have a rectilinear cross-section, but may curve downwardly as they extend outwardly from the belt 14. Ultimately, the cleats 22 are present to push water, and any cross-sectional shape that accomplishes that purpose may be used. Additionally, the cleats 22 need not be continuous bars, they may have different cross-sectional shapes, and they may be inclined at different angles.

Figure 4:
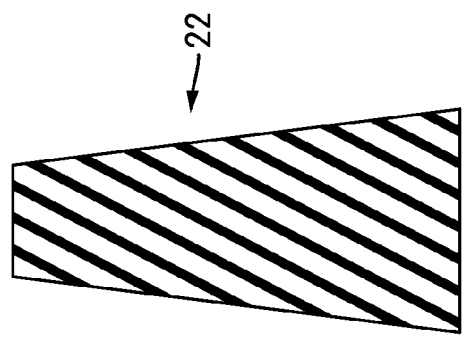
FIG. 4 is a schematic view of the belt of the lateral circulator and one of its cleats, illustrating the forces generated by it.

The forces developed by each cleat 22 are shown in FIG. 4, a schematic view of the belt 14 with only a single cleat 22. If the belt 14 is driven forward with a longitudinal velocity $V_L$, the cleat 22 will generate a forward force ($F_L$) and a forward velocity ($V_L$), as well as a downward force ($F_D$) and a downward velocity ($V_D$). The amount of forward versus downward force (i.e., the forward and downward components of the overall force vector) is in proportion to the inclination angle of the cleat, $\theta$, and can be readily determined trigonometrically. In most embodiments, the angle $\theta$ will be in the range of about 10-45°, although a more preferable range for at least some embodiments might be 10-30°, and in some cases, the range might be narrower still, e.g., 18-22°. The cleat of FIG. 4 is inclined at an angle of 22°, although it should be understood that the angles shown and described above assume that it is desirable to push the water down; if one wished to push the water up, instead of down, the orientation of the cleats 22 would be reversed. In some embodiments, the ratio of $V_D$ to $V_L$ may be, e.g., 3:1, 4:1, etc.

Figure 5:
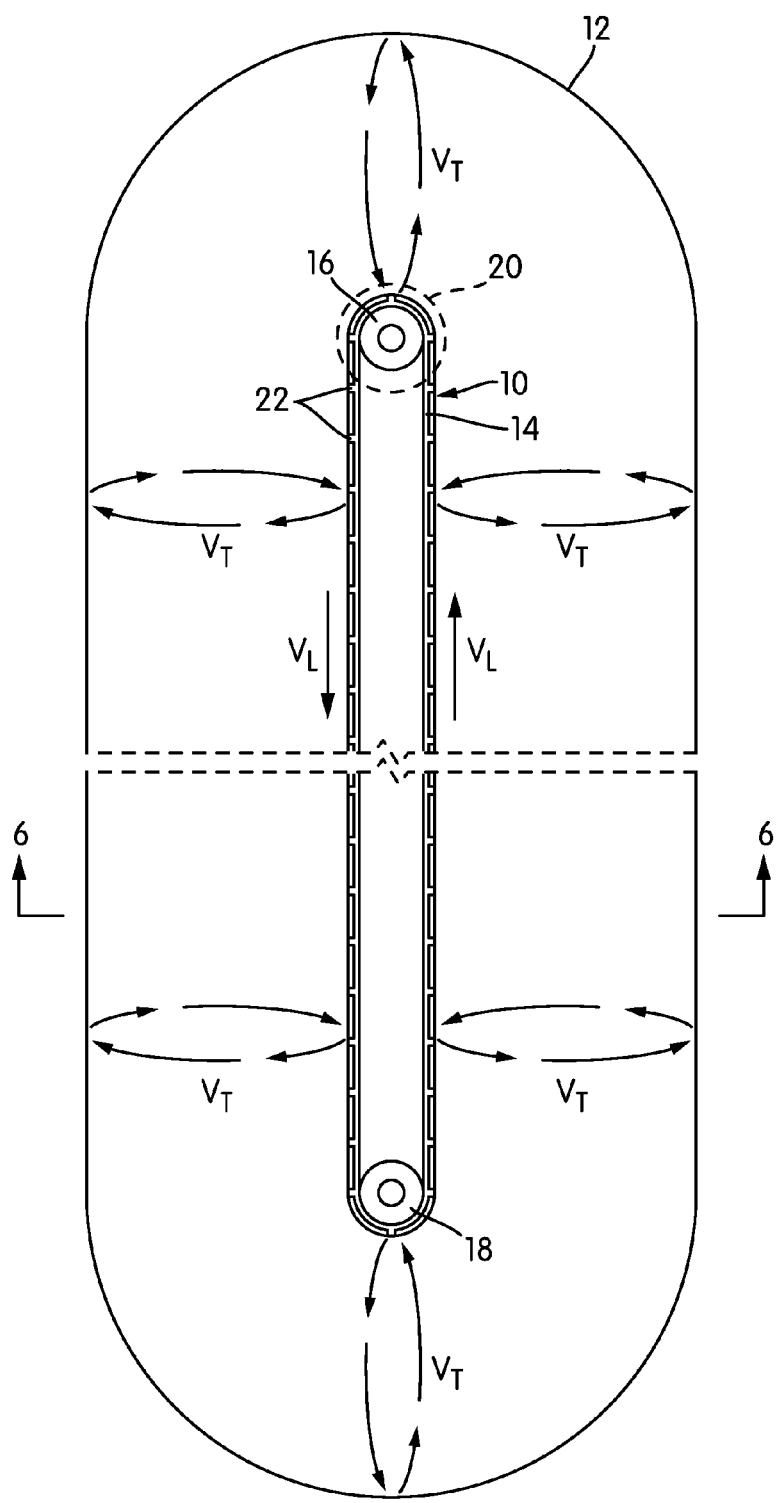
FIG. 5 is a schematic top plan view of the cultivation pond of FIG. 1, illustrating the circulation therein.
Figure 6:
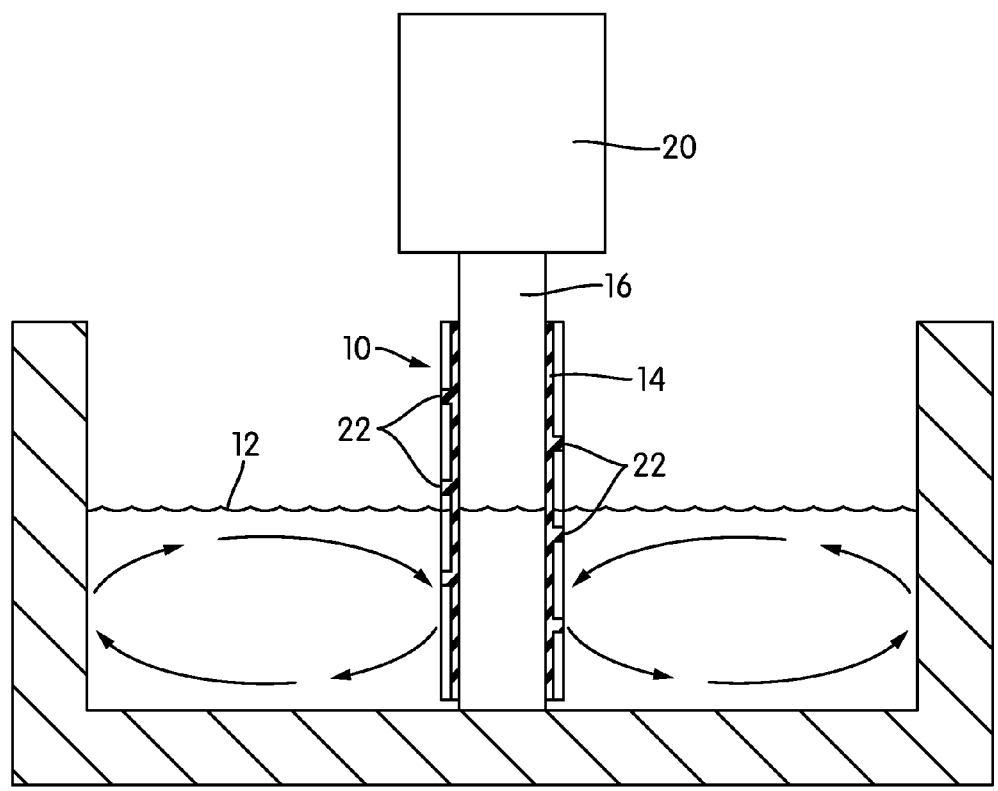
FIG. 6 is a cross-sectional view of the cultivation pond of FIG. 1, taken through Line 6-6 of FIG. 5 and illustrating the circulation within the pond.

FIG. 4 is a two-dimensional schematic illustration of the effect of the cleats 22 on the water. The cross-section of the cleats 22 may be chosen specifically to cast water outward, away from the belt 14. FIG. 5 is a top plan view of the pool 12 and the circulator 10. As shown in FIG. 5, the belt 14 is driven forward at some longitudinal velocity, $V_L$, that is aligned with the central long axis of the pond. However, the motion of the belt 14 also drives water forward, down, and away from the belt 14, creating continuous lateral circulation (i.e., in the direction indicated by arrows $V_T$) between the circulator 10 and the sides and the bottom of the pool 12. FIG. 6 is a cross-sectional view of the pool 12, taken through Line 6-6 of FIG. 5, illustrating the circulation from that perspective.

As FIGS. 5 and 6 make clear, the circulator 10 is not a point-source agitator placed, for example, on one end of the pond 12. Rather, by extending over virtually the entire length of the pond 12, it provides continuous circulation and agitation energy to essentially the entirety of the pond 12. In so doing, it may remove agitation-based size restrictions on cultivation ponds 12. While in many cases, the circulator 10 will be operated continuously, in this context, the term "continuous circulation" to the fact that the circulator 10 spans and is physically continuous over substantially the entirety of the pond 12. The circulation or agitation in the pond 12 is distributed across almost the entire pond 12; the circulator 10 is not a point source for agitation, like a paddlewheel.

In a typical scenario, the belt 14 is driven and the cleats 22 are adapted to ensure a relatively mild turbulent flow in the direction of belt movement, but a relatively strong turbulent flow in the lateral direction. With conventional ponds that use paddlewheels as point-source agitators, Reynolds numbers of 60,000 or more are commonly achieved, indicating very strong turbulent flow. However, large amounts of energy are expended in maintaining those flow conditions, and some of the invested energy may be lost. By contrast, with lateral circulators 10 according to embodiments of the present invention, Reynolds numbers of 15,000-30,000 in the lateral (i.e., transverse) direction may be more commonly used. The belt 22 itself may be driven at relatively low velocity longitudinally, e.g., on the order of 2 inches (5 cm) per second.

As those of skill in the art will realize, the velocity at which the belt 14 is driven and the velocity of the water around the belt 14 are, in many cases, two different things. The degree to which the belt 14 pushes the water, the momentum imparted, and the direction will vary with the drive velocity; the orientation, number, and shape of the cleats 22; and a number of other fluid-dynamic factors. As those of skill in the art might also appreciate, even without cleats 22 to aid in moving water, a belt 14 driven at a high enough velocity could probably produce a desired lateral velocity of the water, but the fraction of that energy that would be transferred to the water would likely be much less than it would be with cleats 22. Ultimately, the desired water velocities will also depend on non-mechanical factors, such as the type of algae or other organism, and the presence of wind and other environmental factors.

As was described above, the belt 14 will typically be given a longitudinal velocity, referred to in this description as $V_L$. While that velocity may be continuous over long periods of time, it need not necessarily be. The overall velocity may be varied from moment to moment, if necessary, based on conditions within the cultivation pond 12, the needs of the particular organism being cultivated, and environmental factors that affect the pond 12. It should also be understood that the speed at which the motor 20 runs may not be equal to $V_L$; in most cases, gearing or a drive train between the motor 20 and the pulley 16 that it drives will alter the speed of the motor 20. In many cases, a gearbox may be integrated into the motor.

Beyond imparting motion to the belt, other drive signals may be used, and in some cases, superposed on the main drive signal that creates the longitudinal velocity of the belt 14. For example, it has long been known that vibrations introduced into mechanical systems can help to prevent friction and make mechanisms operate more smoothly—a technique called dithering. Embodiments of the present invention may use dithering—for example, by altering the velocity, acceleration, or direction of the belt 14 at a rate that is significantly different than the velocity of the belt 14 or the rate at which it drives the water. For example, if $V_L$ is selected to drive the water at a rate of 1 Hz, a lower-amplitude, low frequency signal equivalent to about 0.1 Hz may be used for dithering. The resulting movement may be an oscillation, a vibration, or a non-cyclic pattern of acceleration, velocity, or directional changes. The nature and amplitude of the dithering may vary from embodiment to embodiment, and is not particularly limited, so long as the dithering does not detract from the primary motions that the moving belt 14 is to impart to the water.

Of course, depending on the belt velocity and other factors, dithering may not be required. In a typical embodiment, the turbulent flows that surround the belt 14 and impinge on it during operation may vibrate the circulator 10 in the same way that dithering would—without the need to drive the belt 14 in any special way.

The belt 14 itself may be made in any of a variety of ways. For example, the belt may be made of a rubber, or of a rubberized or coated fabric or other textile. As was described above, the exterior of the belt 14 has cleats in order to better interact with the water in the cultivation pond 12. The inward-facing side of the belt 14 may also have grooves, cleats, or other features in some embodiments. Because the belt 14 is mounted vertically, slippage of the belt 14 on the pulleys 16, 18 may be more of an issue than in a belt 14 of similar dimensions that is mounted horizontally. Thus, grooves, cleats, or other inward-facing gripping features may be helpful in retaining the belt 14 on the pulleys 16, 18. For example, the belt 14 and pulleys 16, 18 may have the cleats and pulley-grooves shown in U.S. Pat. No. 4,011,939 to Conrad, the contents of which are incorporated by reference in their entirety.

Additionally, while the pulleys 16, 18 in the illustrated embodiment are rounded, additional features may be included to prevent slippage or other tracking problems. In some cases, sprockets mounted near or at the edges of the pulleys 16, 18 may be made to insert into series of complementary slots cut or formed in coincident positions near the edges of the belt 14. In other words, the belt 14 and pulleys 16, 18 may have male and female complementary engaging structures to prevent belt slippage and so-called tracking problems. In some cases, the male structures may be carried by the belt 14 and the female structures may be carried by the pulleys 16, 18, while in other cases, the opposite may be true.

Figure 7:
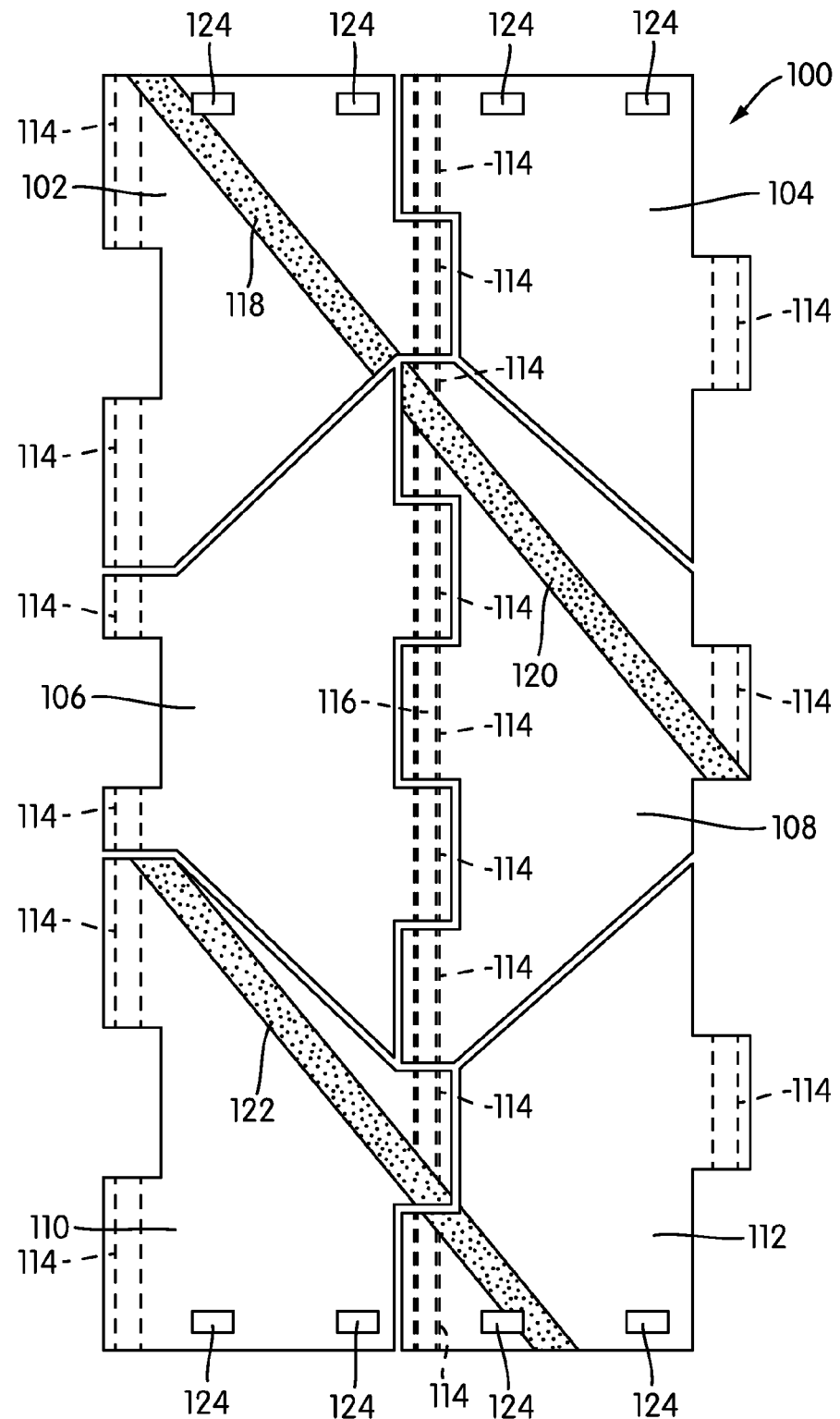
FIG. 7 is an elevational view of a portion of a circulator belt constructed of individual segments, according to another embodiment of the invention.

Belts 14 may also be made of a number of rigid sections of plastic, rubber, or metal connected together to articulate or flex. As one example of this, FIG. 7 is an elevational view of a section of a belt 100, that is comprised of a number of modular sections 102, 104, 106, 108, 110, 112, each of which is rigid or semi-rigid. The sections 102, 104, 106, 108, 110, 112, which are a plurality of interconnected plates or tiles, have edges that define a series of complementary projections and grooves, allowing the sections 102, 104, 106, 108, 110, 112 to be enmeshed in or interconnected with one another. A series of openings 114, which line up when the sections 102, 104, 106, 108, 110, 112 are enmeshed, allow for the insertion of pins 116, about which the sections 102, 104, 106, 108, 110, 112 hinge to allow the belt 100 to flex.

In the description above, it was briefly explained that the cleats 22 need not be continuous bars. On the belt 100, the cleats are not only discontinuous, but portions of them are carried by different sections 102, 108, 110. More specifically, in the illustration of FIG. 7, three cleat sections 118, 120, 122 are each carried by a different section 102, 108, 110 of the belt. The cleat sections 118, 120, 122 have the inclination angle described above, and may have the cross-sectional shape described above or any other desirable shape. As shown, when the sections 102, 108, 110 are assembled, the cleat sections 118, 120, 122 roughly line up, although there may be some discontinuity.

Figure 8:
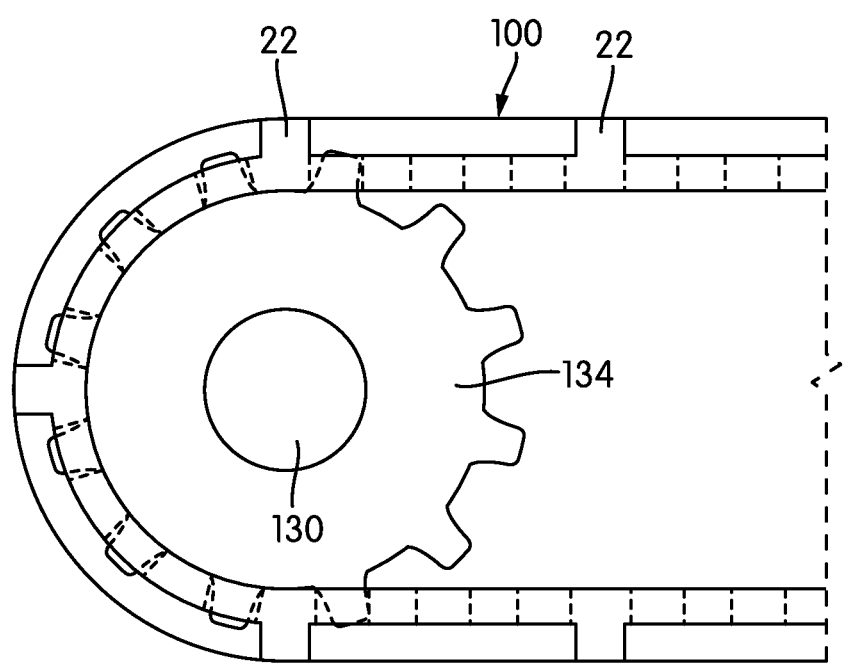
FIG. 8 is a top plan view of the circulator belt of FIG. 7 engaged by a pulley with a sprocket.

Additionally, the two segments 102, 104 that define the top of the belt 100 and the two segments that define the bottom of the belt 100 in the illustration of FIG. 7 include a series of slots 124 at a regular pitch positioned to engage a drive sprocket on one of the belt-drive pulleys. FIG. 8 illustrates the engagement of the belt 100 trained over a pulley 130 with sprockets 134.

Figure 9:
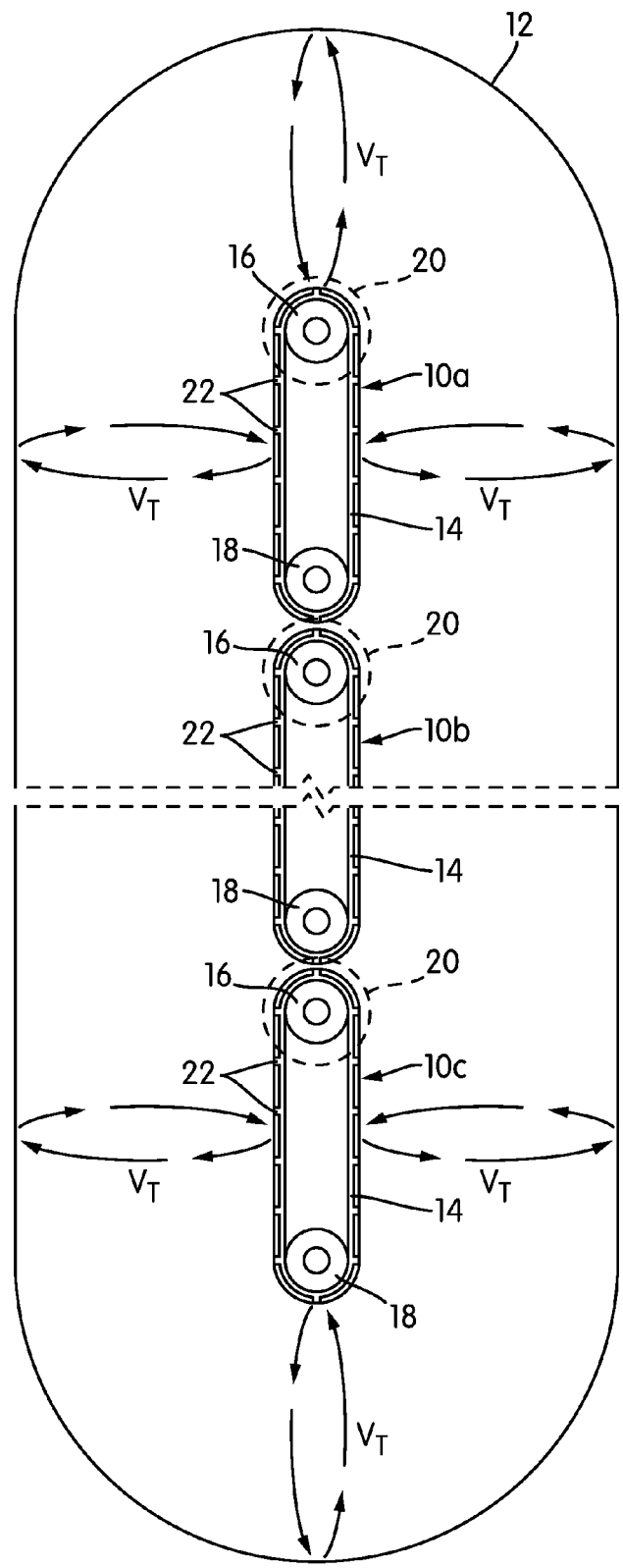
FIG. 9 is a top plan view of a cultivation pond with a circulation system comprised of a number of shorter conveyor belts operating together.

In the description above, a single circulator 10 with a single belt 14, 100 spans the length of the cultivation pond 12. However, that need not be the case in all embodiments. Instead, in some embodiments, multiple circulators arranged in series or, in some cases, in parallel, may be used. FIG. 9 is a top plan view illustrating three circulators 10a, 10b, 10c arranged in series, aligned end-to-end, to cover the same length of a cultivation pond 12. Each of the circulators 10a, 10b, 10c has its own endless belt 14, trained over its own set of pulleys 18, 20. The ends of the circulators 10a, 10b, 10c are spaced closely together, although the spacings may be modified to effect control over circulation in the areas between the circulators 10a, 10b, 10c. Of course, any number of circulators 10a, 10b, 10c may be used to cover any desired length or distance.

Smaller circulators 10a, 10b, 10c may be used in parallel when the cultivation pond, or a channel within the pond, is particularly wide. Circulators 10a, 10b, 10c may also be used in parallel when the pond 12 is divided or partially divided such that a single circulator 10 or in-series line of circulators 10a, 10b, 10c is unlikely to produce a lateral circulation that will reach essentially the entire pond.

Although this description places some emphasis on the circulator 10 providing continuous circulation or agitation across an entire cultivation pond 12, and that arrangement has a number of advantages, it need not be used in that way in all embodiments to be effective. In some cases, a lateral circulator may be considerably shorter than the circulator 10 of FIG. 1. In cases where the circulator is relatively short or small compared to the size of the cultivation pond 12, that circulator essentially becomes a point source for circulation or agitation, in which case, its longitudinal velocity may be significantly greater than a circulator 10 with a more extensive area in order to achieve the same degree of circulation or agitation.

While the invention has been described with respect to certain embodiments, the description is intended to be exemplary, rather than limiting. Modifications and changes may be made within the scope of the invention, which is defined by the appended claims.

What is claimed is:

1. A circulator for a cultivation pond, comprising:
at least one drive pulley oriented vertically and coupled to a motor or to a drivetrain connected to the motor;
at least one second pulley oriented vertically and spaced from the first drive pulley;
an endless belt trained over the at least one drive pulley and the at least one second pulley, such that the breadth of the belt is oriented vertically; and
a plurality of cleats attached to and spaced over the entire area of the belt on an outwardly-facing side thereof, the plurality of cleats being oriented at an angle greater than 0° and less than 90° with respect to the belt, such that as the belt is driven longitudinally along the cultivation pond, a downward force component is imparted to water contacting the cleats;
wherein the downward force component creates a lateral circulation in the cultivation pond.

2. The circulator of claim 1, wherein the plurality of cleats is oriented at an angle between 10° and 45°.

3. The circulator of claim 1, wherein the plurality of cleats is arranged at a regular pitch.

4. The circulator of claim 1, wherein the cleats extend about 1-2 inches outward from the belt.

5. The circulator of claim 1, wherein the belt comprises a rubber or fabric.

6. The circulator of claim 1, wherein the belt comprises a plurality of interconnected plates or tiles.

7. The circulator of claim 1, wherein the at least one drive pulley or the at least one second pulley include a sprocket.

8. The circulator of claim 7, wherein the belt includes slots spaced and positioned to receive the sprocket.

* * * * *